(12) United States Patent
Glinecke et al.

(10) Patent No.: US 6,451,343 B1
(45) Date of Patent: Sep. 17, 2002

(54) COMPOSITION FOR TREATING DEMENTIA AND ALZHEIMER'S DISEASE

(75) Inventors: Robert Glinecke, Pottstown, PA (US); William Muldoon, Philadelphia, PA (US); Susan Marie Milosovich, West Chester, PA (US); Joseph Sauer, Sarasota, FL (US); Laurence Rousseau, Broxbourne (GB)

(73) Assignees: SmithKline Beecham Corporation, Philadelphia, PA (US); SmithKline Beecham p.l.c., Brentford (GB)

(*) Notice: Subject to any disclaimer, the term of this patent is extended or adjusted under 35 U.S.C. 154(b) by 0 days.

(21) Appl. No.: 09/623,213

(22) PCT Filed: Mar. 5, 1999

(86) PCT No.: PCT/EP99/01557

§ 371 (c)(1),
(2), (4) Date: Aug. 30, 2000

(87) PCT Pub. No.: WO99/45924

PCT Pub. Date: Sep. 16, 1999

Related U.S. Application Data

(60) Provisional application No. 60/077,527, filed on Mar. 11, 1998, and provisional application No. 60/077,480, filed on Mar. 11, 1998.

(30) Foreign Application Priority Data

Mar. 11, 1998 (GB) .............................. 9805192

(51) Int. Cl.[7] .............................. A61K 9/40; A61K 9/30; A61K 9/28; A61K 9/22; A61K 9/20

(52) U.S. Cl. ........................ 424/478; 424/464; 424/465; 424/468; 424/474; 424/475; 424/470

(58) Field of Search .................................. 424/451, 464, 424/465, 468, 469, 470

(56) References Cited

U.S. PATENT DOCUMENTS 5,433,951 A * 7/1995 Serajuddin et al. ......... 424/486

FOREIGN PATENT DOCUMENTS

| WO | WO9200737 | 1/1992 |
|----|-----------|--------|
| WO | WO 96/12486 | 5/1996 |
| WO | WO 97/04750 | 2/1997 |
| WO | WO-97/04750 A2 * | 2/1997 |
| WO | WO 98/10762 | 3/1998 |
| WO | WO-98/10762 A2 * | 3/1998 |

* cited by examiner

Primary Examiner—Thurman K. Page
Assistant Examiner—Rachel M. Bennett
(74) Attorney, Agent, or Firm—Linda E. Hall; Stephen A. Venetianer; Charles M. Kinzig

(57) ABSTRACT

Controlled release dosage forms useful in the treatment and/or prophylaxis of dementia, including Alzheimer's disease, in mammals, and for enhancing amyloid precursor protein processing along a non-amyloidogenic pathway in patients suffering from, or at risk of developing, Alzeimer's disease.

27 Claims, No Drawings

COMPOSITION FOR TREATING DEMENTIA AND ALZHEIMER'S DISEASE

This Application is a 371 of PCT/EP99/01557 filed Mar. 3, 1999, which claims benefit of Ser. No. 60/077,527 filed Mar. 11, 1998 and Ser. No. 60/077,480 filed Mar. 11, 1998.

The present invention relates to novel formulations, and to their use in the treatment and/or prophylaxis of certain disorders.

[R-(Z)]-α-(methoxyimino)-α-(1-azabicyclo [2.2.2]oct-3-yl)acetonitrile monohydrochloride (compound X) and methods for its preparation are disclosed in EP-A-0392803, WO95/31456 and WO93/17018. The compound enhances acetylcholine function via an action at muscarinic receptors within the central nervous system, and is therefore of potential use in the treatment and/or prophylaxis of dementia in mammals.

WO96/12486 discloses the use of compound X in the manufacture of a medicament for enhancing amyloid precursor protein processing along a non-amyloidogenic pathway in patients suffering from, or at risk of developing, Alzheimer's disease.

Fast-release swallow tablet and oral solution formulations of compound X both result in rapid absorption of the compound into the circulation, and require twice a day dosing for optimal efficacy.

It has now been surprisingly found that it is possible to formulate compound X, which has very high water solubility and is active at extremely low doses, in such a way that release is controlled to take place over a period of hours. Such a formulation would require dosing only once a day: this is likely to improve compliance in a patient population characterised by poor memory; it may also reduce side-effects in case of accidental overdosing.

Accordingly, in a first aspect the present invention provides a controlled release oral dosage form containing 0.04% w/w pfb compound X and 98.5–99.5% w/w total mono, di and triglycerides and polyethylene glycol mono and diesters consisting of Gelucire 50/13 (EP) and Gelucire 50/02 (Fr Ph) in a ratio of >0.02 Gelucire 50/13 (EP) to Gelucire 50/02 (Fr Ph), in a hard gelatin capsule containing 0.10 mg/capsule compound X pfb, such that the release profile of the capsule in 1 mM HCl is 20–60% after 8 hr.

Preferably the release profile after 8 hr is 20–40% or 30–60%.

Gelucire 50/13 (EP) is a mixture of mono, di and triglycerides and polyethylene glycol mono and diesters specified in the European Pharmacopeia "Stearoyl Macroglycerides" (Supplement 1998) as:

specific mixtures of monoesters, diesters and triesters of glycerol and monoesters and diesters of macrogols with a mean relative molecular mass between 300 and 4000 comprising:
free glycerol content: <3%
lauric acid (C12): <5%
myristic acid (C14): <5%
different nominal amounts of stearic acid (C18) and of palmitic acid (C16). The sum of stearic acid and of palmitic acid is not less than 90%.

Gelucire 50/02 (Fr Ph) is a mixture of mono, di and triglycerides and polyethylene glycol mono and diesters specified in the French Pharmacopoeia "Glycerides Polyglycolyses Satures" (1990) as:

specific mixtures of mono, di and triglycerides and polyethylene glycol mono and diesters, obtained either by partial alcoholysis of hydrogenated vegetable oils using polyethylene glycol of relative molecular weight ranging 200–2000, or by esterification of saturated fatty acids using polyethylene glycol of relative molecular weight ranging 200–2000, comprising:
free glycerol content: <3%
caprylic acid (C8): <15%
capric acid (C10): <15%
lauric acid (C12): <50%
myristic acid (C14): <25%
palmitic acid (C16): <55%
stearic acid (C18): <97%

The mono, di and triglycerides and polyethylene glycol mono and diesters preferably make up 99.41% of the dosage form. The ratio of Gelucire 50/13 (EP) to Gelucire 50/02 (Fr Ph) is preferably <0.055, more preferably ≦0.053.

In a preferred aspect the mixture of mono, di and triglycerides and polyethylene glycol mono and diesters consists of Gelucire 50/13 (Gattefosse) and Gelucire 50/02 (Gattefosse). Most preferably the composition comprises 97.41% Gelucire 50/13 (Gattefosse) and 2.00% Gelucire 50/02 (Gattefosse) or 94.41% Gelucire 50/13 (Gattefosse) and 5.00% Gelucire 50/02 (Gattefosse).

The composition preferably additionally comprises propylene glycol, preferably at 0.45% w/w (1.13 mg/capsule).

The composition preferably additionally comprises 3,4,5-trihydroxybenzoic acid propyl ester, preferably at 0.10% w/w (0.25 mg/capsule).

In a preferred embodiment of the first aspect the composition is selected from:

| Component | % w/w | mg/capsule |
|---|---|---|
| Compound X | 0.04pfb | 0.10pfb |
| Gelucire 50/02 (EP) | 94.41 | 236.00 |
| Gelucire 50/13 (Fr Ph) | 5.00 | 12.50 |
| propylene glycol | 0.45 | 1.13 |
| 3,4,5-trihydroxybenzoic acid propyl ester | 0.10 | 0.25 |
| and | | |
| Compound X | 0.04pfb | 0.10pfb |
| Gelucire 50/02 (EP) | 97.41 | 243.52 |
| Gelucire 50/13 (Fr Ph) | 2.00 | 5.00 |
| propylene glycol | 0.45 | 1.13 |
| 3,4,5-trihydroxybenzoic acid propyl ester | 0.10 | 0.25 | in a hard gelatin capsule.

In a second aspect, the present invention provides a controlled release oral dosage form containing compound X of the following composition:

| Ingredient | mg/tablet | %/tablet |
|---|---|---|
| Compound X | 0.005–0.1 pfb | |
| hydroxypropyl methylcellulose | 37.5–45 | 25–30 |
| dibasic calcium phosphate dihydrate | 45–52.5 | 30–35 |
| microcrystalline cellulose (nominal mean particle size 50 microns) | 19.5 | 13.0 |
| microcrystalline cellulose (nominal mean particle size 100 microns) | 37.76 | 25.2 | granulated, compressed into tablets and coated to a 3% weight gain with a seal coat consisting of a solution of hydroxypropyl methylcellulose aqueous dispersion with plasticizer in purified water at 10% solids followed by a coat consisting of ethylcellulose aqueous dispersion with oleic acid, ammonium hydroxide and plasticizer or a mixture of ethylcellulose aqueous dispersion with oleic acid, ammonium hydroxide and plasticizer and hydroxypropylmethylcellulose aqueous dispersion with polytheylene glycol plasticizer, such that 40–65% of the drug is released within 8 hours in water.

The composition preferably additionally comprises: sodium dihydrogen citrate, preferably at a level of 1.50 mg/tablet (1.0%) and/or magnesium stearate, preferably at a level of 1.125 mg/tablet (0.75%).

In preferred embodiments of the second aspect:

hydroxpropyl methylcellulose is Methocel E4M CR;

microcrystalline cellulose (nominal mean particle size 50 microns) is Avicel PH101;

microcrystalline cellulose (nominal mean particle size 100 microns) is Avicel PH102;

hydroxypropyl methylcellulose aqueous dispersion has polyethylene glycol plasticizer and is preferably Opadry White or Opadry Clear (YS-1-9025A); and/or ethylcellulose aqueous dispersion has fractionated coconut oil plasticizer and is preferably Surelease Clear (E-7-19010).

In a third aspect, the present invention provides a controlled release oral dosage form containing compound X of the following composition:

| Ingredient | mg/tablet | %/tablet |
|---|---|---|
| Compound X | 0.005–0.1 pfb | |
| ethylcellulose | 22.5–37.5 | 15–25 |
| dibasic calcium phosphate dihydrate | 63.3–78.3 | 42.2–52.2 |
| microcrystalline cellulose | 30.0–40.0 | 19.8–26.7 | compressed into tablets and coated to a 3% weight gain with a seal coating solution consisting of hydroxymethylcellulose aqueous dispersion with plasticizer in purified water at 10% solids concentration followed by a coat consisting of ethylcellulose aqueous dispersion with oleic acid, ammonium hydroxide and plasticizer or a mixture of ethylcellulose aqueous dispersion with oleic acid, ammonium hydroxide and and hydroxypropylmethylcellulose aqueous dispersion with plasticizer.

In one preferred embodiment of the third aspect the composition additionally comprises sodium dihydrogen citrate, preferably at a level of 3.00 mg/tablet (2.0%) and/or colloidal silicon dioxide, preferably at a level of 0.75 mg/tablet (0.50%) and/or magnesium stearate, preferably at a level of 1.125 mg/tablet (0.75%) and/or the microcrystalline cellulose has a mean particle size of 100 microns, preferably at a level of 32.5 mg/tablet (21.7%); and coated to a 3% weight gain with a seal coating solution consisting of hydroxymethylcellulose aqueous dispersion with plasticizer in purified water at 10% solids concentration followed by a coat consisting of ethylcellulose aqueous dispersion with oleic acid, ammonium hydroxide and plasticizer or a mixture of ethylcellulose aqueous dispersion with oleic acid, ammonium hydroxide and plasticizer and hydroxypropylmethylcellulose aqueous dispersion with polytheylene glycol plasticizer, such that 35–50% of the drug is released within 8 hours in water.

In a second preferred embodiment of the third aspect the composition is wet granulated before compression using an ethyl cellulose aqueous dispersion containing oleic acid, ammonium hydroxide and plasticizer, preferably at a level of 7.5–15.0 mg/tablet (5.0–10.0%). Where the composition is wet granulated, it additionally comprises sodium dihydrogen citrate, preferably at a level of 1.50 mg/tablet (1.0%), and/or magnesium stearate, preferably at a level of 1.25 mg/tablet (0.75%), and/or the micorcrystalline cellulose has a mean particle size of 50 microns, preferably at a level of 37.5 mg/tablet (25%); and coated to a 3% weight gain with a seal coating solution consisting of hydroxymethylcellulose aqueous dispersion with plasticizer in purified water at 10% solids concentration followed by a coat consisting of ethylcellulose aqueous dispersion with oleic acid, ammonium hydroxide and plasticizer or a mixture of ethylcellulose aqueous dispersion with oleic acid, ammonium hydroxide and plasticizer and hydroxypropylmethylcellulose aqueous dispersion with plasticizer such that 60–75% of the drug is released within 8 hours in water.

In preferred embodiments of the third aspect:

ethylcellulose is Ethocel Std 7;

microcrystalline cellulose (nominal mean particle size 50 microns) is Avicel PH101;

microcrystalline cellulose (nominal mean particle size 100 microns) is Avicel PH102;

hydroxypropyl methylcellulose aqueous dispersion has polyethylene glycol plasticizer and is preferably Opadry Clear (YS-1-9025A); and/or ethylcellulose aqueous dispersion has fractionated coconut oil plasticizer and is preferably Surelease Clear (E-7-19010).

By controlled release is meant release of the active substance from the dosage form is modified to occur at a slower rate than that from an immediate release product, such as a conventional swallow tablet or capsule.

The dosage form of the invention may be used in the treatment and/or prophylaxis of dementia, including Alzheimer's disease, in mammals, and/or for enhancing amyloid precursor protein processing along a non-amyloidogenic pathway in patients suffering from, or at risk of developing, Alzheimer's disease. These disorders are herein after referred to as "the Disorders".

The present invention provides a method of treating "the Disorders" by administering an effective amount of the controlled release oral dosage form of the invention to a sufferer in need thereof.

The present invention further provides the use of a controlled release oral dosage form of the invention in the manufacture of a medicament for treating "the Disorders".

The present invention also provides a pharmaceutical composition for use in the treatment of "the Disorders" which comprises a controlled release oral dosage form of the invention.

The following example illustrates the present invention. The weight shown is the weight of free base (pfb=pure free base). Mesh sizes are U.S. standard.

EXAMPLE 1

| Component | % w/w | mg/capsule | Function |
|---|---|---|---|
| Compound X | 0.04 pfb | 0.10 pfb | Active |
| Gelucire 50/02* | 94.41 | 236.00 | Wax matrix |
| Gelucire 50/13* | 5.00 | 12.50 | Wax matrix |
| propylene glycol | 0.45 | 1.13 | Solvent |
| propyl gallate** | 0.10 | 0.25 | Antioxidant |

EXAMPLE 2

| Component | % w/w | mg/capsule | Function |
|---|---|---|---|
| Compound X | 0.04 pfb | 0.10 pfb | Active |
| Gelucire 50/02* | 97.41 | 243.52 | Wax matrix |
| Gelucire 50/13* | 2.00 | 5.00 | Wax matrix |
| propylene glycol | 0.45 | 1.13 | Solvent |
| propyl gallate** | 0.10 | 0.25 | Antioxidant |

*specific mixture of mono, di and triglycerides, and polyethylene glycol mono and diesters of the following compositions:

Gelucire 50/13 (Gattefosse, certificate of analysis):
Free glycerol content: <3%
Caprylic acid: <3%
Capric acid: <3%
Lauric acid: <5%
Myristic acid: <5%
Palmitic acid: 40–50%
Stearic acid: 48–58%

Gelucire 50/02 (Gattefosse, certificate of analysis):
Free glycerol content: <3%
Caprylic acid: <3%
Capric acid: <3%
Lauric acid: 4–14%
Myristic acid: 2–12%
Palmitic acid: 32–42%
Stearic acid: 3747%

**3,4,5-trihydroxybenzoic acid propyl ester

Process for Examples 1 and 2:

Waxes were melted together at around 60 degrees C and mixed with propyl gallate. Compound X was dissolved in propylene glycol, and blended into the waxes. The mixture was filled into size 3 hard gelatin capsule shells.

Release Profiles

Dissolution equipment conforming to an apparatus No.2 of USP.
Medium: 1 mM HCl.
Volume: 500 mL
Temperature: 37 C.
Paddle speed: 50 rpm.

TABLE 1

Release Profile of wax-filled capsules of Example 1

| Time (hr) | % Released |
|---|---|
| 2 | 17 |
| 4 | 27 |
| 8 | 46 |
| 15 | 70 |
| 23 | 86 |

TABLE 2

Release Profile of wax-filled capsules of Example 2

| Time (hr) | % Released |
|---|---|
| 2 | 10 |
| 4 | 18 |
| 8 | 29 |

TABLE 2-continued

Release Profile of wax-filled capsules of Example 2

| Time (hr) | % Released |
|---|---|
| 15 | 44 |
| 23 | 56 |

EXAMPLE 3

| Ingredient | mg/tablet | Function |
|---|---|---|
| Compound X | 0.005–0.1 pfb | Active |
| Methocel E4M CR | 37.5 | Hydrogel matrix |
| sodium dihydrogen citrate | 1.50 | Stabilizer |
| dibasic calcium phosphate dihydrate | 52.5 | Hydrophobic diluent |
| Avicel PH101 | 19.5 | Hydrophobic diluent |
| Avicel PH102 | 37.76 | Hydrophobic diluent |
| magnesium stearate | 1.125 | Lubricant |
| purified water | q.s. | |

Tablets were prepared by the following procedure:

1. Preblend the drug with a small quantity of the excipients
2. Wet granulate using high shear granulation
3. Dry granulation using fluid bed or oven process
4. Screen through a comminuting mill
5. Blend the remaining excipients with the drug granluation
6. Lubricate with magnesium stearate
7. Compress into tablets
8. Coat tablets with polymer Seal Coating Solution:

A solution of Opadry Clear (YS-1-9025A) in purified water at 10% solids concentrations was made by dissolving 100 grams of Opadry Clear into 900 grams of purified water.

Polymer Coating:

A polymer coating dispersion containing ethylcellulose (Surelease Clear (E-7-19010)) and Opadry Clear (YS-1-9025A) of the following composition was made and used for polymer coating the seal coated beads at 4–5% weight gain.

| Component | % w/w | Function |
|---|---|---|
| Surelease Clear (E-7-19010) | 4.5 (25% as solids) | Release controlling polymer coat with plasticiser |
| Opadry Clear (YS-1-9025A) | 0.5 | Release controlling polymer coat |
| Purified water | q.s. | |
| Total | 100 | |

700 grams of core tablets were coated using a Vector LDCS pan to a 3% weight gain with the Opadry Clear (YS-1-9025A) seal coating solution. The seal coated tablets were then polymer coated to 4–5% weight gain using the Surelease/Opadry coating dispersion.

TABLE 3

Release Profile for tablet of Example 3 of Compound X in water

| Time (hr) | % Dissolved 4% coat | % Dissolved 5% coat |
|---|---|---|
| 1 | 0.14 | 0.17 |
| 2 | 0.61 | 0.35 |
| 4 | 19.9 | 6.6 |
| 8 | 62 | 52 |
| 12 | 87 | 92 |

EXAMPLE 4

| Ingredient | mg/tablet | Function |
|---|---|---|
| Compound X | 0.005–0.1 pfb | Active |
| Ethocel Std 7 | 30.0 | Hydrogel matrix |
| sodium dihydrogen citrate | 1.50 | Stabilizer |
| dibasic calcium phosphate dihydrate | 70.76 | Hydrophobic diluent |
| Avicel PH101 | 37.5 | Hydrophobic diluent |
| Surelease Clear (E-7-19010) | 9.0 | Hydrogel matrix |
| magnesium stearate | 1.125 | Lubricant |

Tablets were prepared by the following procedure:

1. Preblend the drug with a small quantity of the excipients
2. Granulate mix with Surelease dispersion using high shear granulation and wet screen resulting granulation
3. Dry granulation using fluid bed
4. Screen through a sizing mill
5. Blend the remaining excipients with the drug granluation
6. Lubricate with magnesium stearate
7. Compress into tablets
8. Coat tablets with polymer Seal coating solution: A solution of Opadry Clear (YS-1-9025A) in purified water at 10% solids concentrations was made by dissolving 100 grams of Opadry Clear into 900 grams of purified water.

Polymer Coating: A polymer coating dispersion containing ethylcellulose (Surelease (E-7-19010) and Opadry Clear (YS-1-9025A) of the following composition was made and used for polymer coating the seal coated tablets at 4–5% weight gain.

| Component | % w/w | Function |
|---|---|---|
| Surelease Clear (E-7-19010) | 4.25 (25% as solids) | Release controlling polymer coat with plasticiser |
| Opadry Clear (YS-1-9025A) | 0.75 | Release controlling polymer coat |
| purified water | q.s. | |
| Total | 100 | |

700 grams of core tablets were coated using a Vector LDCS pan to a 3% weight gain with the Opadry Clear seal coating solution. The seal coated tablets were then polymer coated to 4–5% weight gain using the Surelease/Opadry coating dispersion.

TABLE 4

Release Profile for the tablet of Example 4 of Compound X in water

| Time (hr) | % Dissolved 4% coat | % Dissolved 5% coat |
|---|---|---|
| 1 | 2.1 | 0.57 |
| 2 | 7.4 | 3.1 |
| 4 | 35 | 26 |
| 8 | 73 | 71 |
| 12 | 90 | 88 |

EXAMPLE 5

| Ingredient | mg/tablet | Function |
|---|---|---|
| Compound X | 0.005–0.1 pfb | Active |
| Ethocel Std 7 | 37.5 | Hydrogel matrix |
| sodium dihydrogen citrate | 3.00 | Stabilizer |
| dibasic calcium phosphate dihydrate | 75.0 | Hydrophobic diluent |
| Avicel PH102 | 32.5 | Hydrophobic diluent |
| colloidal silicon dioxide | 0.75 | Glidant |
| magnesium stearate | 1.125 | Lubicant |

Tablets were prepared by the following procedure:

1. Preblend the drug with a small quantity of the excipients
2. Blend the remaining excipients with the drug preblend
3. Lubricate with magnesium stearate
4. Compress into tablets
5. Coat tablets with polymer Seal coating solution: A solution of Opadry Clear (YS-1-9025A) in purified water at 10% solids concentrations was made by dissolving 100 grams of Opadry Clear into 900 grams of purified water.

Polymer Coating: A polymer coating dispersion containing ethylcellulose (Surelease (E-7-19010)) and Opadry Clear (YS-1-9025A) of the following composition was made and used for polymer coating the seal coated tablets at 4% weight gain.

| Component | % w/w | Function |
|---|---|---|
| Surelease Clear (E-7-19010) | 3.4 (25% as solids) | Release controlling polymer coat with plasticiser |
| Opadry Clear (YS-1-9025A) | 0.6 | Release controlling polymer coat |
| purified water | q.s. | |
| Total | 100 | |

700 grams of core tablets were coated using a Vector LDCS pan to a 3% weight gain with the Opadry Clear seal coating solution. The seal coated tablets were then polymer coated to 4% weight gain using the Surelease/Opadry coating dispersion.

TABLE 5

Release Profile for tablet of Example 5 of Compound X in water

| Time (hr) | % Dissolved |
|---|---|
| 2 | 6.2 |
| 4 | 14 |
| 8 | 38 |
| 12 | 66 |
| 16 | 90 |

| Tradename | Generic description | Supplier |
|---|---|---|
| Ethocel Std 7 | ethylcellulose (viscosity 5% w/v solution of 6.4 mPa mean particle size 210 microns) | Dow |
| Methocel E4M CR | hydroxpropyl methcellulose (nominal viscosity, 2% in water, of 4000) % methoxyl = 28–30, 95% < 100 mesh) | Dow |
| Avicel PH101 | microcrystalline cellulose (nominal mean particle size 50 microns) | FMC Corp |
| Avicel PH102 | microcrystalline cellulose (nominal mean particle size 100 microns) | FMC Corp |
| Opadry Clear (YS-1-9025A) | hydroxymethylcellulose aqueous dispersion with polyethylene glycol plasticizer | Colorcon |
| Surelease Clear (E-7-19010) | aqueous dispersion of ethyl cellulose oleic acid ammonium hydroxide fractionated coconut oil plasticizer | Colorcon |

What is claimed is:

1. A controlled release oral dosage form containing [R-(Z)]-α-(methoxyimino)-α-(1-azabicyclo[2.2.2]oct-3-yl) acetonitrile monohydrochloride (compound X) of the following composition:

| Ingredient | mg/tablet | %/tablet |
|---|---|---|
| Compound X | 0.005–0.1 pfb | |
| ethylcellulose | 22.5–37.5 | 15–25 |
| dibasic calcium phosphate dihydrate | 63.3–78.3 | 42.2–52.2 |
| microcrystalline cellulose | 30.0–40.0 | 19.8–26.7 | compressed into tablets and coated to a 3% weight gain with a seal coating solution consisting of hydroxymethylcellulose aqueous dispersion with plasticizer in purified water at 10% solids concentration followed by a coat consisting of ethylcellulose aqueous dispersion with oleic acid, ammonium hydroxide and plasticizer or a mixture of ethylcellulose aqueous dispersion with oleic acid, ammonium hydroxide and hydroxypropylmethylcellulose aqueous dispersion with plasticizer.

2. A dosage form according to claim 1 which additionally comprises sodium dihydrogen citrate and/or colloidal silicon dioxide and/or magnesium stearate and/or the microcrystalline cellulose has a mean particle size of 100 microns; and coated to a 3% weight gain with a seal coating solution consisting of hydroxymethylcellulose aqueous dispersion with plasticizer in purified water at 10% solids concentration followed by a coat consisting of ethylcellulose aqueous dispersion with oleic acid, ammonium hydroxide and plasticizer or a mixture of ethylcellulose aqueous dispersion with oleic acid, ammonium hydroxide and plasticizer and hydroxypropylmethylcellulose aqueous dispersion with polyethylene glycol plasticizer, such that 35–50% of the drug is released within 8 hours in water.

3. A dosage form according to claim 2 which comprises sodium dihydrogen citrate at a level of 3.00 mg/tablet (2.0%) and/or colloidal silicon dioxide at a level of 0.75 mg/tablet (0.50%) and/or magnesium stearate at a level of 1.125 mg/tablet (0.75%) and/or microcrystalline cellulose at a level of 32.5 mg/tablet (21.7%).

4. A dosage form according to claim 1 wherein the composition is wet granulated before compression using an ethyl cellulose aqueous dispersion containing oleic acid, ammonium hydroxide and plasticizer.

5. A dosage form according to claim 4 wherein the ethyl cellulose dispersion is at a level of 7.5–15.0 mg/tablet (5.0–10.0%).

6. A dosage form according to claim 4 which additionally comprises sodium dihydrogen citrate and/or magnesium stearate and/or the microcrystalline cellulose has a mean particle size of 50 microns; and coated to a 3% weight gain with a seal coating solution consisting of hydroxymethylcellulose aqueous dispersion with plasticizer in purified water at 10% solids concentration followed by a coat consisting of ethylcellulose aqueous dispersion with oleic acid, ammonium hydroxide and plasticizer or a mixture of ethylcellulose aqueous dispersion with oleic acid, ammonium hydroxide and plasticizer and hydroxypropylmethylcellulose aqueous dispersion with plasticizer such that 60–75% of the drug is released within 8 hours in water.

7. A dosage form according to claim 6 which comprises sodium dihydrogen citrate at a level of 1.50 mg/tablet (1.0%) and/or magnesium stearate at a level of 1.125 mg/tablet (0.75%) and/or microcrystalline cellulose at a level of 37.5 mg/tablet (25%).

8. A dosage form according to claim 1 wherein the hydroxypropyl methylcellulose aqueous dispersion has polyethylene glycol plasticizer and/or the ethylcellulose aqueous dispersion has fractionated coconut oil plasticizer.

9. A controlled release oral dosage form according to claim 1 of the following composition:

| Ingredient | mg/tablet |
|---|---|
| Compound X | 0.005–0.1 pfb |
| Ethylcellulose, (viscosity 5% w/v solution of 6.4 mPa, mean particle size 210 microns) | 30.0 |
| sodium dihydrogen citrate | 1.50 |
| dibasic calcium phosphate dihydrate | 70.76 |
| microcrystalline cellulose (nominal mean particle size 50 microns) | 37.5 |
| ethylcellulose aqueous dispersion, with oleic acid, ammonium hydroxide, and fractionated coconut oil plasticizer | 9.0 |
| magnesium stearate | 1.125 |

Seal coating solution: A solution of hydroxymethylcellulose aqueous dispersion with polyethylene glycol plasticizer in purified water at 10% solids concentrations made by dissolving 100 grams of the of hydroxymethylcellulose aqueous dispersion with polyethylene glycol plasticizer into 900 grams of purified water (to 3% weight gain); polymer coating: (4–5% weight gain)

| Component | % w/w |
|---|---|
| ethylcellulose aqueous dispersion, with oleic acid, ammonium hydroxide | 4.25 (25% as solids) |

-continued

| Component | % w/w |
|---|---|
| and fractionated coconut oil plasticizer | |
| hydroxymethylcellulose aqueous dispersion with polyethylene glycol plasticizer | 0.75 |
| purified water | q.s. |
| Total | 100. |

10. A controlled release oral dosage form according to claim 1 of the following composition:

| Ingredient | mg/tablet | Function |
|---|---|---|
| Compound X | 0.005–0.1 pfb | Active |
| Ethylcellulose (viscosity 5% w/v solution of 6.4 mPa, mean particle size 210 microns) | 37.5 | Hydrogel matrix |
| sodium dihydrogen citrate | 3.00 | Stabilizer |
| dibasic calcium phosphate dihydrate | 75.0 | Hydrophobic diluent |
| microcrystalline cellulose (nominal mean particle size 100 microns) | 32.5 | Hydrophobic diluent |
| colloidal silicon dioxide | 0.75 | Glidant |
| magnesium stearate | 1.125 | Lubricant |

Seal coating solution: A solution of hydroxymethylcellulose aqueous dispersion with polyethylene glycol plasticizer in purified water at 10% solids concentrations made by dissolving 100 grams of the hydroxymethylcellulose aqueous dispersion with polyethylene glycol plasticizer into 900 grams of purified water (to 3% weight gain);
Polymer Coating: (4% weight gain):

| Component | % w/w |
|---|---|
| ethylcellulose aqueous dispersion, with oleic acid, ammonium hydroxide, and fractionated coconut oil plasticizer | 3.4 (25% as solids) |
| hydroxymethylcellulose aqueous dispersion with polyethylene glycol plasticizer | 0.6 |
| purified water | q.s. |
| Total | 100. |

11. A controlled release oral dosage form containing [R-(Z)]-α-(methoxyimino)-α-(1-azabicyclo [2.2.2]oct-3-yl) acetonitrile monohydrochloride (compound X) of the following composition:

| Ingredient | mg/tablet | %/tablet |
|---|---|---|
| Compound X | 0.005–0.1 pfb | |
| hydroxypropyl methylcellulose | 37.5–45 | 25–30 |
| dibasic calcium phosphate dihydrate | 45–52.5 | 30–35 |
| microcrystalline cellulose (nominal mean particle size 50 microns) | 19.5 | 13.0 |
| microcrystalline cellulose (nominal mean particle size 100 microns) | 37.76 | 25.2 | granulated, compressed into tablets and coated to a 3% weight gain with a seal coat consisting of a solution of hydroxypropyl methylcellulose aqueous dispersion with plasticizer in purified water at 10% solids followed by a coat consisting of ethylcellulose aqueous dispersion with oleic acid, ammonium hydroxide and plasticizer or a mixture of ethylcellulose aqueous dispersion with oleic acid, ammonium hydroxide and plasticizer and hydroxypropylmethylcellulose aqueous dispersion with polyethylene glycol plasticizer, such that 40–65% of the drug is released within 8 hours in water.

12. A dosage form according to claim 11 which additionally comprises:
sodium dihydrogen citrate and/or magnesium stearate.

13. A dosage form according to claim 12 which comprises sodium dihydrogen citrate at a level of 1.50 mg/tablet (1.0%) and/or magnesium stearate at a level of 1.125 mg/tablet (0.75%).

14. A dosage form according to claim 11 wherein the hydroxypropyl methylcellulose aqueous dispersion has polyethylene glycol plasticizer and/or the ethylcellulose aqueous dispersion has fractionated coconut oil plasticizer.

15. A controlled release oral dosage form according to claim 11 of the following composition:

| Ingredient | mg/tablet |
|---|---|
| Compound X | 0.005–0.1 pfb |
| hydroxypropyl methcellulose (nominal viscosity, 2% in water, of 4000, % methoxyl = 28–30, 95% < 100 mesh) | 37.5 |
| sodium dihydrogen citrate | 1.50 |
| dibasic calcium phosphate dihydrate | 52.5 |
| microcrystalline cellulose (nominal mean particle size 50 microns) | 19.5 |
| microcrystalline cellulose (nominal mean particle size 100 microns) | 37.76 |
| magnesium stearate | 1.125 |
| purified water | q.s. |

Seal coating solution: A solution of hydroxymethylcellulose aqueous dispersion with polyethylene glycol plasticizer in purified water at 10% solids concentrations made by dissolving 100 grams of hydroxymethylcellulose aqueous dispersion with polyethylene glycol plasticizer into 900 grams of purified water;
Polymer Coating (4–5% weight gain):

| Component | % w/w |
|---|---|
| ethylcellulose aqueous dispersion, with oleic acid, ammonium hydroxide, and fractionated coconut oil plasticizer | 4.5 (25% as solids) |
| hydroxymethylcellulose aqueous dispersion with polyethylene glycol plasticizer | 0.5 |
| Purified water | q.s. |
| Total | 100. |

16. A controlled release oral dosage form containing 0.04% w/w pfb [R-(Z)]-α-(methoxyimino)-α-(1-azabicyclo [2.2.2]oct-3-yl)acetonitrile monohydrochloride (compound X) and 98.5–99.5% w/w total mono, di and triglycerides and polyethylene glycol mono and diesters consisting of:
(A) specific mixtures of monoesters, diesters and triesters of glycerol and monoesters and diesters of macrogols with a mean relative molecular mass between 300 and 4000 comprising:
free glycerol content: <3%
lauric acid (C12): <5%
myristic acid (C14): <5%
different nominal amounts of stearic acid (C18) and of palmitic acid (C16) wherein the sum of stearic acid and of palmitic acid is not less than 90%; and (B) specific mixtures of mono, di and triglycerides and polyethylene glycol mono and diesters, obtained either by partial alcoholysis of hydrogenated vegetable oils using polyethylene glycol of relative molecular weight ranging 200–2000, or by esterification of saturated fatty acids using polyethylene glycol of relative molecular weight ranging 200–2000, comprising:
free glycerol content: <3%
caprylic acid (C8): <15%
capric acid (C10): <15%
lauric acid (C12): <50%
myristic acid (C14): <25%
palimitic acid (C16): <55%
stearic acid (C18): <97% in a ratio of >0.02 (A) to (B) in a hard gelatin capsule containing 0.10 mg/capsule compound X pfb, such that the release profile of the capsule in 1 mM HCl is 20–60% after 8 hr.

17. A dosage form according to claim 16 wherein the release profile after 8 hr is 20–40% or 30–60%.

18. A dosage form according to claim 16 which comprises 97.41% (B) and 2.00% (A) or 94.41% (B) and 5.00% (A).

19. A dosage form according to claim 16 which additionally comprises propylene glycol.

20. A dosage form according to claim 19 which comprises propylene glycol at 0.45% w/w.

21. A dosage form according to claim 16 which additionally comprises 3,4,5-trihydroxybenzoic acid propyl ester.

22. A dosage form according to claim 21 which comprises 3,4,5-trihydroxybenzoic acid propyl ester at 0.10% w/w.

23. A dosage form according to claim 16 selected from:

| Component | % w/w | mg/capsule |
|---|---|---|
| Compound X | 0.04 pfb | 0.10 pfb |
| specific mixtures of mono, di and triglycerides and polyethylene glycol mono and diesters, of the following compositions: | 94.41 | 236.00 |
| Free glycerol content: <3% Caprylic acid: <3% Capric acid: <3% Lauric acid: 4–14% Myristic acid: 2–12% Palmitic acid: 32–42% Stearic acid: 37–47% | | |
| specific mixtures of mono, di and triglycerides, and polyethylene glycol mono and diesters of the following compositions: | 5.00 | 12.50 |
| Free glycerol content: <3% Caprylic acid: <3% Capric acid: <3% Lauric acid: <5% Myristic acid: <5% Palmitic acid: 40–50% Stearic acid: 48–58% | | |
| propylene glycol | 0.45 | 1.13 |
| 3,4,5-trihydroxybenzoic acid propyl ester | 0.10 | 0.25 |
| and | | |
| Compound X | 0.04 pfb | 0.10 pfb |
| specific mixtures of mono, di and triglycerides and polyethylene glycol mono and diesters, of the following compositions: | 97.41 | 243.52 |
| Free glycerol content: <3% Caprylic acid: <3% Capric acid: <3% Lauric acid: 4–14% Myristic acid: 2–12% Palmitic acid: 32–42% Stearic acid: 37–47% | | |
| specific mixtures of mono, di and triglycerides, and polyethylene glycol mono and diesters of the following compositions: | 2.00 | 5.00 |
| Free glycerol content: <3% Caprylic acid: <3% Capric acid: <3% Lauric acid: <5% Myristic acid: <5% Palmitic acid: 40–50% Stearic acid: 48–58% | | |
| propylene glycol | 0.45 | 1.13 |
| 3,4,5-trihydroxybenzoic acid propyl ester in a hard gelatin capsule. | 0.10 | 0.25 |

24. A process for preparing a dosage form as defined in claim 1 which process comprises admixing the ingredients.

25. A method of treatment and/or prophylaxis of dementia and Alzheimer's disease, in mammals, and/or for enhancing amyloid precursor protein processing along a non-amyloidogenic pathway in patients suffering from, or at risk of developing, Alzheimer's disease by administering an effective amount of the dosage form of claim 1 to a sufferer in need thereof.

26. A method of treatment and/or prophylaxis of dementia and Alzheimer's disease, in mammals, and/or for enhancing amyloid precursor protein processing along a non-amyloidogenic pathway in patients suffering from, or at risk of developing, Alzheimer's disease by administering an effective amount of the dosage form of claim 11 to a sufferer in need thereof.

27. A method of treatment and/or prophylaxis of dementia and Alzheimer's disease, in mammals, and/or for enhancing amyloid precursor protein processing along a non-amyloidogenic pathway in patients suffering from, or at risk of developing, Alzheimer's disease by administering an effective amount of the dosage form of claim 16 to a sufferer in need thereof.

* * * * *